(12) United States Patent
Kim et al.

(10) Patent No.: US 9,131,483 B2
(45) Date of Patent: Sep. 8, 2015

(54) METHOD AND APPARATUS FOR TRANSRECEIVING DATA IN MEDICAL BODY AREA NETWORK

(75) Inventors: Suhwook Kim, Gyeonggi-do (KR);
Bonghoe Kim, Gyeonggi-do (KR);
Jaewon Lim, Gyeonggi-do (KR)

(73) Assignee: LG Electronics Inc., Seoul (KR)

( * ) Notice: Subject to any disclaimer, the term of this patent is extended or adjusted under 35 U.S.C. 154(b) by 142 days.

(21) Appl. No.: 14/000,932

(22) PCT Filed: Dec. 20, 2011

(86) PCT No.: PCT/KR2011/009844
§ 371 (c)(1),
(2), (4) Date: Aug. 22, 2013

(87) PCT Pub. No.: WO2012/121476
PCT Pub. Date: Sep. 13, 2012

(65) Prior Publication Data
US 2013/0329690 A1    Dec. 12, 2013

Related U.S. Application Data

(60) Provisional application No. 61/451,542, filed on Mar. 10, 2011, provisional application No. 61/483,069, filed on May 6, 2011, provisional application No. 61/485,101, filed on May 11, 2011.

(51) Int. Cl.
*G06F 11/00* (2006.01)
*H04L 1/00* (2006.01)
(Continued)

(52) U.S. Cl.
CPC .......... *H04W 72/0406* (2013.01); *A61B 5/0028* (2013.01); *H04W 36/0072* (2013.01); *H04W 48/14* (2013.01); *H04W 36/06* (2013.01)

(58) Field of Classification Search
CPC .......... H04W 36/072; H04W 72/0406; H04W 48/14; A61B 5/0028
USPC .......... 370/329, 328, 252, 254, 330, 253, 392, 370/351
See application file for complete search history.

(56) References Cited

U.S. PATENT DOCUMENTS

| 8,995,361 B2 * | 3/2015 | Nguyen et al. ................. 370/329 |
| 9,014,190 B2 * | 4/2015 | Nguyen et al. ................. 370/392 |

(Continued)

FOREIGN PATENT DOCUMENTS

| JP | 2008-522703 A | 7/2008 |
| KR | 10-2009-0011863 A | 2/2009 |
| KR | 10-2009-0117003 A | 11/2009 |

OTHER PUBLICATIONS

Written Opinion issued in corresponding International Patent Application No. PCT/KR2011/009844 dated May 30, 2012.

(Continued)

*Primary Examiner* — Chuong T Ho
(74) *Attorney, Agent, or Firm* — Morgan, Lewis & Bockius LLP

(57) ABSTRACT

The present invention relates to a method for a terminal transreceiving data with a base station in a medical body area network (MBAN) comprising the following steps: receiving from the base station information on an available channel list, which shows at least one available channel from a second frequency band, through a first frequency band; channel switching from one channel from the first frequency band to one of the available channels from the second frequency band based on the information on the available channel list; and transreceiving data with the base station through the available channel to which the channel is switched.

18 Claims, 10 Drawing Sheets

(51) Int. Cl.
*H04L 12/26* (2006.01)
*H04W 72/04* (2009.01)
*H04W 36/00* (2009.01)
*A61B 5/00* (2006.01)
*H04W 48/14* (2009.01)
*H04W 36/06* (2009.01)

(56) References Cited

U.S. PATENT DOCUMENTS

2009/0231125 A1  9/2009  Baldus et al.
2011/0149759 A1* 6/2011  Jollota ......................... 370/252
2011/0249631 A1* 10/2011 Li et al. ....................... 370/329
2011/0267958 A1* 11/2011 Sekiya et al. ................ 370/241
2013/0121178 A1* 5/2013  Mainaud et al. ............. 370/252
2013/0281142 A1* 10/2013 Li et al. ....................... 455/500

OTHER PUBLICATIONS

International Search Report issued in corresponding International Patent Application No. PCT/KR2011/009844 dated May 30, 2012.

* cited by examiner

Base Station

Terminal (a)    (b)

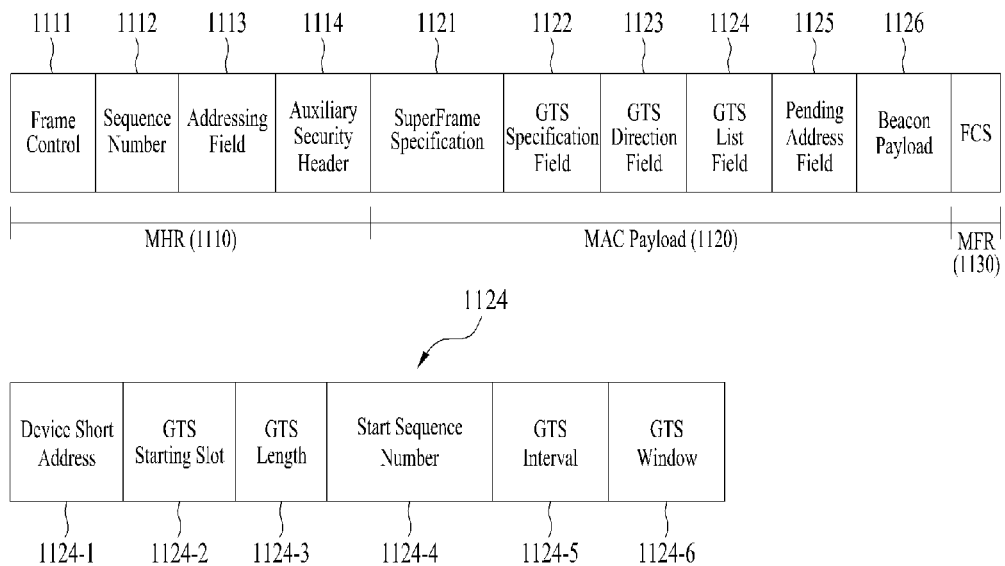

METHOD AND APPARATUS FOR TRANSRECEIVING DATA IN MEDICAL BODY AREA NETWORK

TECHNICAL FIELD

The present invention relates to a medical body area network (MBAN), in particular, to a method and apparatus for transceiving data through channel switching.

BACKGROUND ART

IEEE 802.15.4 defines the physical layer (PHY) and medium access control (MAC) sublayer specifications for low-data-rate wireless personal area network (LR-WPAN). IEEE 802.15.4 has some similarities to IEEE 802.15.3 that is a standard for higher-data-rate WPANs.

IEEE 802.15.4 standard uses binary phase-shift keying (BPSK) in a band of 868/915 MHz to provide transmission speed of 20 Kbps and 40 Kbps and uses offset quadrature phase-shift keying (O-QPSK) in a band of 2.45 GHz to provide transmission speed of 250 Kbps. IEEE 802.15.4b standard also uses O-QPSK in a band of 868/915 MHz to provide transmission speed of 250 Kbps.

Unlike wireless local area network (WLANs), access in WPANs is efficiently achieved even in an environment that does not or rarely involves an infrastructure. This feature allows a compact, power efficient, and low-cost solution to act on a wide range of devices.

Medical body area network (MBAN), as an example of WPAN, is being discussed in IEEE 802.15.4.

MBAN (Medical Body Area Network)

A medical body area network (MBAN) system operates in a US frequency band of 2360 MHz to 2400 MHz and is limited to a maximum emission bandwidth of 5 MHz.

A frequency band of 2360 MHz to 2400 MHz used in the MBAN system is already allocated for other wireless communication systems. The MBAN system operates on a cognitive radio-based secondary basis. That is, the MBAN system must not cause harmful interference to a primary user and needs to use the above frequency band despite interference from the primary user.

Thus, when the MBAN system operates in a frequency band of 2360 MHz to 2390 MHz, MBAN devices need to operate inside registered healthcare facilities, in principle.

In collaboration with the primary user, the MBAN system needs to control usage in 2360 MHz to 2390 MHz. When the primary user uses the above frequency band, all operations in the above frequency band need to be initialized and to be restarted using a frequency band of 2390 MHz to 2400 MHz.

That is, when MBAN devices move outdoors, the MBAN devices need to stop an operation or to change the frequency band to 2390 MHz to 2400 MHz used as a basic frequency band and to perform communication. When the MBAN devices operate in a frequency band of 2390 MHz to 2400 MHz, the MBAN devices may perform communication both indoors and outdoors.

When the MBAN devices operate in a frequency band of 2360 MHz to 2390 MHz, transmission power thereof is set to a smallest value of 1 mW and 10*log(B) dBm. When the MBAN devices operate in a frequency band of 2390 MHz to 2400 MHz, the MBAN devices use transmission power of a smallest value of 20 mW and 10*log(B) dBm. Here, B is the 20 dB emission bandwidth.

DISCLOSURE

Technical Problem

As described above, when a medical body area network (MBAN) system operates in a frequency band of 2360 MHz to 2390 MHz, a terminal operates as a secondary user, and thus, a base station cannot periodically transmit a beacon frame via a channel that is used by a primary user. However, although the base station cannot transmit the beacon frame, terminals that want to newly enter the MBAN system unnecessarily perform scanning on all channels and consume power. In addition, terminals are not allowed to perform active scanning in a MBAN band, and thus, time for first access to the MBAN system is relatively increased.

Accordingly, an object of the present invention devised to solve the problem lies in a method in which a terminal associates with a base station in a band of 2390 MHz to 2400 MHz and then receives an available channel list in a band of 2360 MHz to 2390 MHz to reform association with the base station via a channel in a band of 2360 MHz to 2390 MHz.

Technical Solution

The object of the present invention can be achieved by providing a method of transmitting and receiving data by a terminal with a base station in a medical body area network (MBAN), the method including receiving available channel list information from the base station via a channel of a first frequency band, the available channel list information indicating at least one available channel of a second frequency band, performing channel switching from the channel of the first frequency band to one of the at least available channel of the second frequency band, based on the available channel list information, and communicating data with the base station via the channel-switched available channel.

The communicating of the data may further include setting association with the base station, wherein the setting of the association may include transmitting an association request message to the base station, and receiving an association response message corresponding to the association request message from the base station The method may further include receiving a beacon frame from the base station via the channel of the first frequency band.

The available channel list information may be received via the beacon frame.

The method may further include transmitting to the base station an electronic key request message for requesting available channel information of the second frequency band, and receiving from the base station an electronic key response message in response to the electronic key request message, wherein the available channel list information may be contained in the electronic key response message.

The method may further include setting association with the base station in the first frequency band, wherein the setting of the association may include transmitting an association request message to the base station via the channel of the first frequency band, and receiving an association response message corresponding to the association request message from the base station via the channel of the first frequency band.

The available channel list information may include information regarding a bitmap, a center frequency and bandwidth of each available channel, or a start frequency and end frequency of each available channel.

The available channel list information may be included in a MAC payload of the beacon frame.

The method may further include receiving from the base station valid time duration information representing available time of an available channel of the second frequency band.

The valid time duration information may be received after the available channel list information.

The first frequency band may be in a range of 2390 MHz to 2400 MHz, the second frequency band is in a range of 2360 MHz to 2390 MHz, and the channel has 5 MHz.

The electronic key response message may include personal area network identifier (PAN ID) information representing a wireless personal area network (WPAN) using a specific channel of the second frequency band and transmit power limit information representing maximum transmission power in a specific channel of the second frequency band.

The object of the present invention can be achieved by providing a terminal for transmitting and receiving data with a base station in a medical body area network (MBAN), the terminal including a radio frequency unit for transmitting and receiving a radio signal to and from an outside, and a controller connected to the radio frequency unit, wherein the controller controls the radio frequency unit to receive available channel list information, the available channel list information indicating at least one available channel of a second frequency band, performs channel switching from the channel of the first frequency band to one of the at least one available channel of the second frequency band, based on the available channel list information, and controls the radio frequency unit to communicate data with the base station via the channel-switched available channel.

The controller may control the radio frequency unit to receive from the base station valid time duration information representing available time of an available channel of the second frequency band.

Advantageous Effects

According to the disclosure, an available channel list of a band of 2360 MHz to 2390 MHz is received in a frequency band of 2390 to 2400 MHz, and thus, association with a base station may be formed via a channel in a frequency band of 2360 MHz to 2390 MHz without receiving a beacon frame from the base station in a frequency band of 2360 MHz to 2390 MHz.

DESCRIPTION OF DRAWINGS

FIG. 10B illustrates an example of a format of a beacon frame of IEEE 802.15.4 to which an embodiment of the present invention is applicable;

FIG. 11 is a diagram illustrating an example of a frame control field in the frame format illustrated in FIG. 10A;

FIG. 12 illustrates an example of a MAC command frame format of IEEE 802.15.4 to which an embodiment of the present invention is applicable;

BEST MODE

Figure 1:
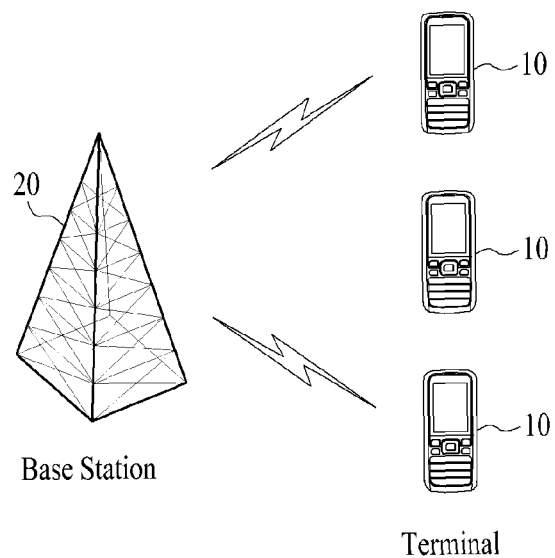
FIG. 1 is a conceptual diagram of a medical body area network (MBAN) system to which an embodiment of the disclosure is applicable.
Figure 2:
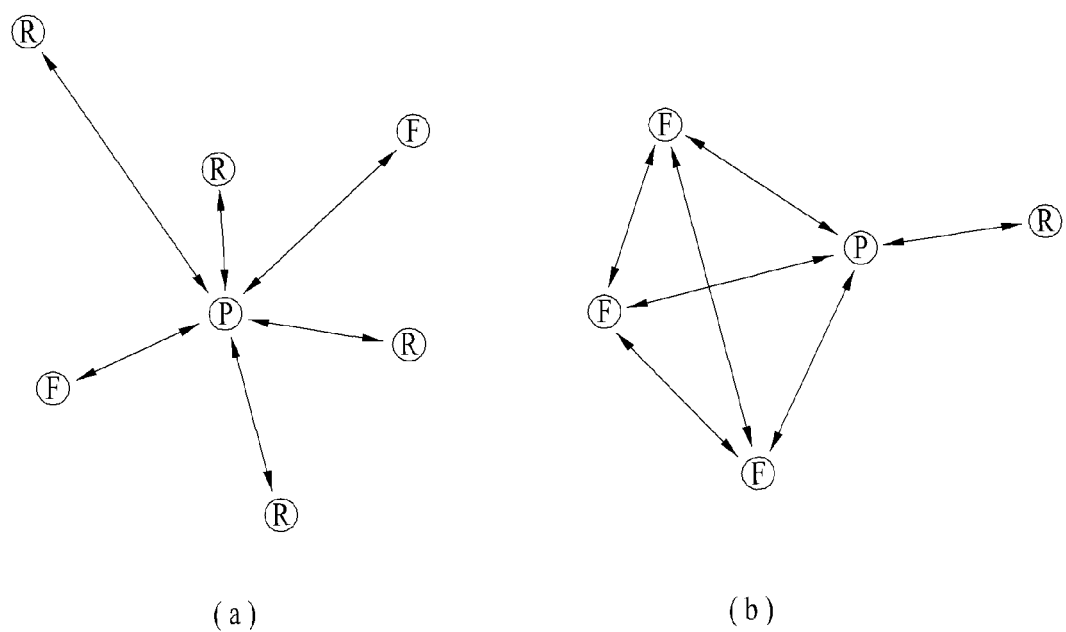
FIGS. 2(A) and 2(B) illustrate examples of IEEE 802.15.4 network topology to which an embodiment of the disclosure is applicable.

The terminology used herein is for the purpose of describing particular embodiments only and is not intended to limit of the present invention. Unless otherwise defined, all technical terms used herein have the same meaning as commonly understood by one of ordinary skill in the art to which this present invention pertains and will not be interpreted in an overly wide or narrow sense unless expressly so defined herein. If a term used herein is a wrong term by which one of ordinary skill in the art cannot correctly understand the present invention, the wrong term should be replaced by a technical term by which one of ordinary skill in the art can correctly understand the present invention. It will be further understood that terms, such as those defined in commonly used dictionaries, should be interpreted as having a meaning that is consistent with their meaning in the context of the relevant art and will not be interpreted in an overly narrow sense.

As used herein, the singular forms "a," "an" and "the" are intended to include the plural forms as well, unless context clearly indicates otherwise. It will be further understood that the terms "comprises" or "comprising" are not intended to included all elements or all steps described herein, but do not preclude exclusion of some elements or steps described herein or addition of one or more other elements or steps.

In addition, the suffixes "module" and "unit" of elements herein are used for convenience of description and thus can be used interchangeably and do not have any distinguishable meanings or functions.

It will be understood that, although the terms first, second, third etc. may be used herein to describe various elements, these elements should not be limited by these terms. These terms are used only to distinguish one element from another element. For example, a first element may be termed a second element and a second element may be termed a first element without departing from the teachings of the present invention.

Reference will now be made in detail to the embodiments of the present invention, examples of which are illustrated in the accompanying drawings, wherein like reference numerals refer to like elements throughout, and a repeated explanation thereof will not be given.

In the description of the present invention, certain detailed explanations of related art are omitted when it is deemed that they may unnecessarily obscure the essence of the invention. The features of the present invention will be more clearly understood from the accompanying drawings but should not be limited by the accompanying drawings.

Embodiments of the disclosure can be supported by standard documents for IEEE 802.15.4-based systems that are low-rate wireless personal area network (LR-WPAN) systems or standard documents for at least one of an IEEE 802 system, 3GPP system, 3GPP LTE and LTE-Advanced (LTE-A) system, and 3GPP2 system for wireless access. That is, steps or features that are not described can be supported by the above documents in order to clearly comprehend the features of the present invention in the embodiments of the disclosure. In addition, terminology used herein can be understood based on the standard documents.

Hereinafter, embodiments of the disclosure will be described in terms of IEEE 802.15.4 standard, but are not limited thereto.

FIG. 1 is a conceptual diagram of a medical body area network (MBAN) system to which an embodiment of the disclosure is applicable.

Referring to FIG. 1, the MBAN system includes a terminal 10 and a base station 20. A plurality of base stations and a plurality of terminals may be present in the MBAN system. Terminals having various capabilities may be added to the MBAN system in order to support additional operations.

The terminal 10 may be fixed or may have mobility and may be denoted by other terms such as UE (User Equipment), user terminal (UT), subscriber station (SS), wireless device, advanced mobile station (AMS), MTC terminal, M2M terminal, device, apparatus, PAN device, MBAN device, PAN MBAN device, full function device (FFD), reduced function device (RFD), etc.

As a type of the terminal described in the disclosure, a personal digital assistant (PDA), a cellular phone, a personal communication service (PCS) phone, a global system for mobile (GSM) phone, a wideband CDMA (WCDMA) phone, a mobile broadband system (MBS) phone, a hand-held PC, a notebook PC, a smart phone, a multi mode-multi band (MM-MB) terminal, etc. may be used.

Here, the smart phone may be a terminal obtained by combining advantages of the terminal and a personal portable terminal and may refer to a terminal obtained by integrating data communication functions of the personal portable terminal, such as schedule management, facsimile transmission/reception, Internet access, etc. into the terminal. In addition, the MM-MB terminal is a terminal that includes a multi-modem chip installed therein to be operable in a portable Internet system and other mobile communication systems (for example, a code division multiple access (CDMA) 2000 system, a wideband CDMA (WCDMA), etc.).

The base station 20 may be a point that communicates with the terminal 10 and is fixed or has mobility and may be denoted by other terms such as NodeB, base transceiver system (BTS), access point (AP), coordinator, PAN coordinator, MBAN coordinator, PAN MBAN coordinator, etc.

Hereinafter, a description of an IEEE 802.15.4 WPAN will be given with reference to FIGS. 2 to 12.

IEEE 802.15.4 Network Topology

FIGS. 2(A) and 2(B) illustrate examples of IEEE 802.15.4 network topology to which an embodiment of the disclosure is applicable. In detail, FIG. 2(A) illustrates star topology and FIG. 2(B) illustrates peer-to-peer topology.

First, two types of devices, full function devices (FFDs) and reduced function devices (RFDs), may participate in a network based on the IEEE 802.15.4 standard.

The FFD is a full function device. For example, the FFD may communicate with an FFD or an RFD and may perform a function such as network initialization, node management, node information storage, etc. In particular, among FFDs, an FFD that operates such that other devices configure a network is referred to as a personal area network (PAN) coordinator (hereinafter, referred to as a coordinator). Thus, network topology that will be described below may be configured by the FFD acting as the coordinator.

However, the RFD performs reduced functions compared with functions of the FFD. In particular, an opposing device with which the RFD communicates is limited to an FFD. Thus, the RFD cannot act as a coordinator. Thus, the FFD may be wholly responsible for a network function such that the RFD may have a stack structure with a small size and may conserve computing/memory resources. In particular, the RFD may be disconnected from a coordinator to enter a save (sleep) mode immediately after searching for a coordinator and transmitting data to the coordinator, and thus, may have significantly reduced power consumption and may operate for a long time using battery power.

In FIGS. 2(A) and 2(B), a device indicated by "F" denotes an FFD, a device indicated by "R" denotes an RFD, and a device indicated by "P" denotes an FFD acting as a coordinator.

Network topology is controlled by one task of a MAC sub layer. Star and peer-to-peer topologies are two topologies that are well known in communication networks and both the topologies are provided by IEEE 802.15.4.

Both the network topologies illustrated in FIGS. 2(A) and 2(B) distinguish between two basic types of network nodes, that is, devices and coordinators.

As illustrated in FIG. 2(A), in the star topology, a plurality of devices 11 communicates directly with a central coordinator 10. In this case, the devices may each be a start point or end point of communication, whereas the coordinate may be a start point, an end point, or a router.

As illustrated in FIG. 2(B), in the peer-to-peer topology, communication between a device 11A and the coordinator 10 is performed along one or more hops using central devices 11B and 11C acting as a relay. Here, each device may communicate with any other device in a network and may configure a more complex type of network such as a mesh network. Here, the coordinator functions as an access point to upper layers. In case of WSN, the coordinator functions as a sink for data collected by sensors.

The star topology may manage devices so as to maintain long operation under battery power. The peer-to-peer topology may configure one or more data transmission paths, thereby achieving high data reliability and connection recognition rate.

In addition, the star topology may have a very limited communication range (several meters). The peer-to-peer topology may allow communication with a large coverage area. Topology may be dynamic, and thus, may change when devices are added or leave a network.

For example, in case of MBAN, the star topology may be suitable for a case in which a coordinator is provided to a place (e.g., a hospital bed) of each patient so as to exchange signals with devices related to one patient. The peer-to-peer topology may be more suitable when one coordinator is provided to serve a plurality of patients (the coordinator may be positioned at a fixed location within a ward).

Thus, in general, the devices 10 may be mobile, whereas the coordinator may be mobile or fixed. The peer-to-peer topology may be more suitable for an environment that changes quickly and is required to quickly set up or change a network or to allow self-organization and self-healing of a network. The self-healing may include establishment of a new coordinator when an existing coordinator is in the event of a fault or leaves a network.

A plurality of star and/or peer-to-peer topologies in which devices have their own respective coordinators may be set up in the same place in a hospital. In this case, individual coordinators may work together so as to prevent mutual interference and to allow sharing or collation of data. According to IEEE 802.15.4, such a network is referred to as 'cluster'. In this regard, overall coordinators are established for clusters and provision for division and aggregation of clusters is performed.

IEEE 802.15.4 Protocol Stack

Figure 3:
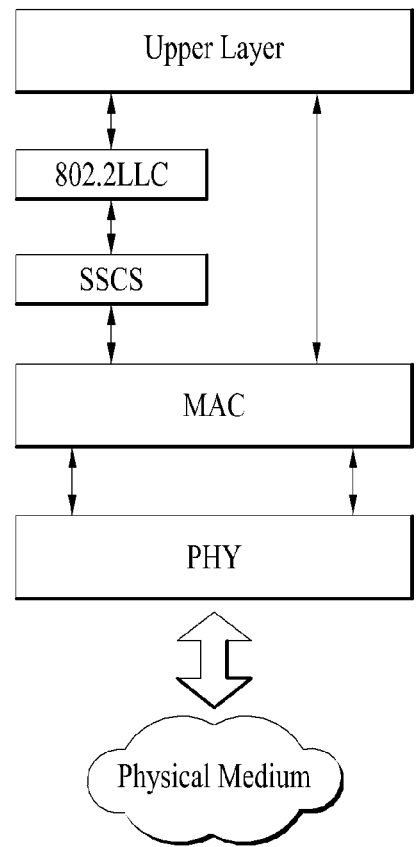
FIG. 3 is a view illustrating the IEEE 802.15.4 protocol stack to which an embodiment of the disclosure is applicable.

FIG. 3 is a view illustrating the IEEE 802.15.4 protocol stack to which an embodiment of the disclosure is applicable.

As seen from FIG. 3, the protocol stack includes a physical (PHY) layer, a medium access control (MAC) layer, and an upper layer.

The PHY layer includes a radio frequency (RF) transceiver and a related control mechanism. The PHY layer may provide a PHY data service for transceiving PHY protocol data units (PHY PDUs) via a physical channel and a PHY management service for management of the PHY layer.

The MAC layer provides access to a physical channel for data transmission. The MAC layer may provide a MAC data service for transceiving MAC protocol data units (MAC PDUs) via the PHY layer and a MAC management service for management of the MAC layer. The MAC layer may perform functions such as beacon management, channel access, GTS management, frame acknowledgement, security functions, etc.

The upper layer includes a network layer and an application layer. The network layer provides functions such as network configuration, processing, message routing, etc. The application layer provides a target function of a device. For example, an IEEE 802.15.4 device 100 may function as a reduced function device (RFD), a full function device (FFD), or a coordinator according to a type of program installed therein, that is, a type of program for processing the application layer.

Figure 4:
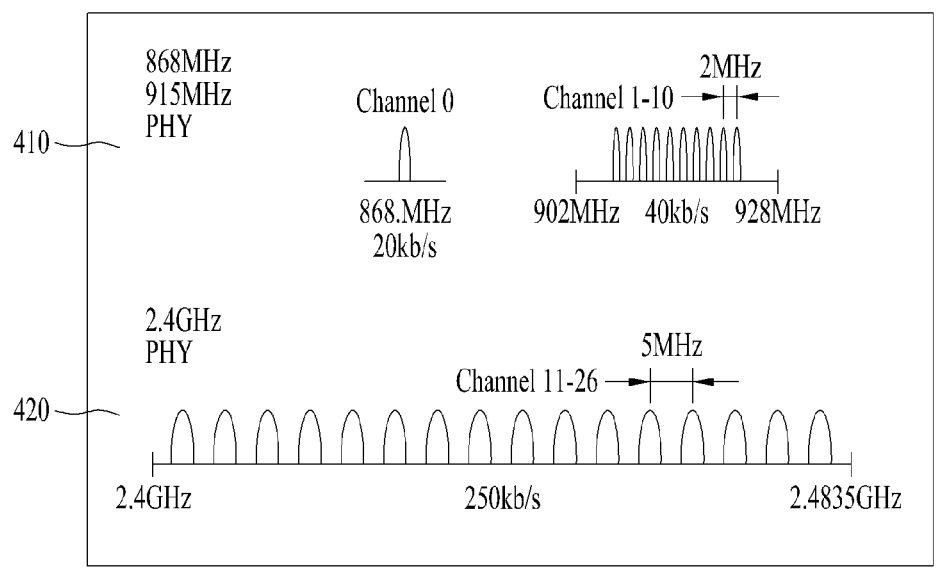
FIG. 4 is a view illustrating available physical (PHY) bands of IEEE 802.15.4 to which an embodiment of the disclosure is applicable.

FIG. 4 is a view illustrating available PHY bands of IEEE 802.15.4 to which an embodiment of the disclosure is applicable.

As illustrated in FIG. 4, two frequency bands 410 and 420 for PHY are present. The low frequency band 410 provides one 20 kb/s channel centered at a frequency of 868.3 MHz and ten 40 kb/s channels centered at a frequency of 915 MHz. The high frequency band 420 provides sixteen 250 kb/s channels centered at a frequency of 2.44 GHz.

As seen from FIG. 4, an IEEE 802.15.4 system operating in a band of 2400 MHz has a channel spacing of 5 MHz.

An MBAN system based on the IEEE 802.15.4 system uses a band of 2360 MHz to 2390 MHz and a band of 2390 MHz to 2400 MHz. A band of 2360 to 2390 MHz is used when a channel is allocated to an MBAN device and the MBAN device operates in healthcare facilities.

A band of 2390 to 2400 MHz is used when an MBAN terminal cannot receive information regarding an MBAN channel from an MBAN coordinator or the MBAN terminal and coordinator operate outside healthcare facilities. In addition, a band 2390 to 2400 MHz may be used as a basic channel band of an MBAN system.

Superframe Structure of IEEE 802.15.4

Figure 5:
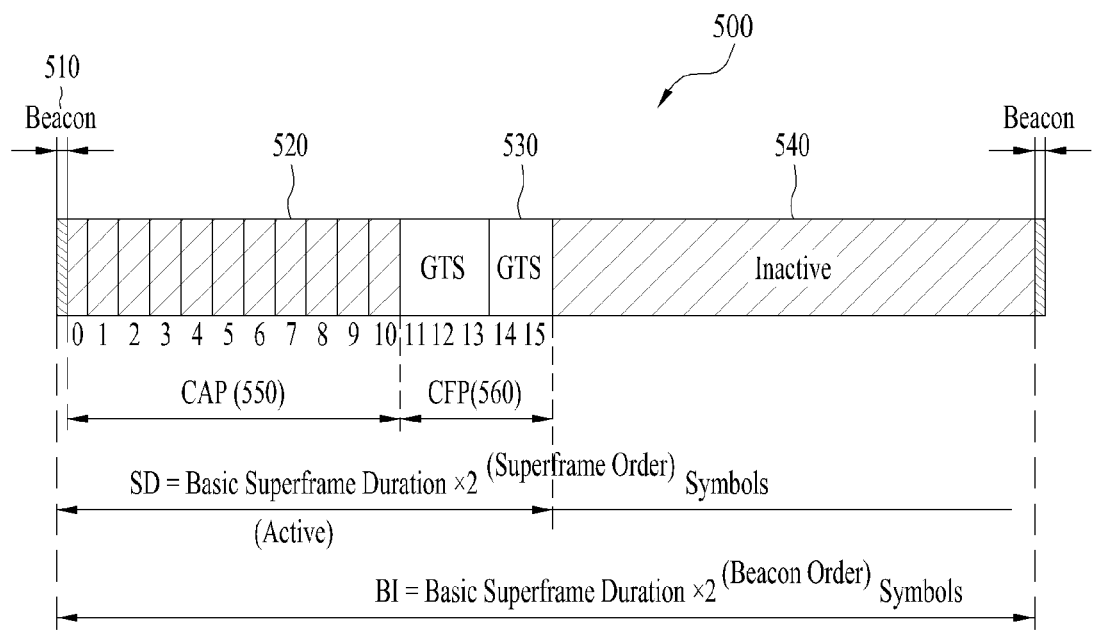
FIG. 5 is a view illustrating an example of a superframe structure of IEEE 802.15.4 to which an embodiment of the disclosure is applicable.

FIG. 5 is a view illustrating an example of a superframe structure of IEEE 802.15.4 to which an embodiment of the disclosure is applicable.

First, IEEE 802.15.4 defines beacon-enabled and non beacon-enabled operations.

In a beacon-enabled network, a coordinator periodically transmits a beacon, and devices are synchronized with the network and periodically listen to the beacon in order to access a channel. Channel access is performed by sequentially transmitting frames in "frame units" in a "superframe" according to the superframe structure defined by the coordinator, as illustrated in FIG. 5.

Each superframe 500 includes two portions, namely, an active portion and an inactive portion. The active portion is divided into a contention access period (CAP) 550 and a contention free period (CFP) 560 subsequent thereto, for guaranteed access for applications having service quality requirements.

As illustrated in FIG. 5, the superframe is divided into 16 equally-spaced time slots when a data frame can be transmitted from a coordinator or a device. Thus, considering devices related to one coordinator, only one device may communicate with a coordinator at one time for each consecutive time slot in the superframe.

First, a slot 510 for a beacon frame transmitted from the coordinator is positioned.

Then, a plurality of slots 520 is provided in the CAP 550 so as to allow data to be transmitted from or to devices based on contention according to a known CSMA-CA algorithm. Briefly, according to CSMA-CA, whenever a device wants transmission, the device waits for a random duration. Subsequent to random backoff, when it is determined that a channel is in a sleep mode, the device transmits its own data. Subsequent to the random backoff, when it is determined that the channel is in a busy mode, the device waits for another random duration before retrying to access the channel.

Then, one or more guaranteed time slots 530 of the CFP 560 are subsequent to the slots 520. Each guaranteed time slot 530 may extend across more than one basic time slot. As suggested from the term CFP, these GTSs may be reserved by a coordinator so as to be exclusively used based on TDMA by a network device, instead of contending with network devices.

However, allocation of GTS may vary every superframe. After an inactive period 540 is terminated, a next superframe is marked by a coordinator that transmits another beacon frame 510. Devices may enter a sleep mode for the inactive period 540 of the superframe. Thus, the length of the inactive period 540 may be extended to conserve device battery power for as long as possible.

In a non beacon-enabled network, a coordinator does not have to transmit a beacon for synchronization as long as the coordinator is not requested to transmit the beacon (for example, for network discovery). Channel access is not limited by superframe structure. In addition, devices are asynchronous and thus perform all data transmission according to CSMA-CA. Devices that do not have data to be transmitted may remain in an idle ("sleep") mode most of times, and a coordinator positions a wake up preamble in front of each data frame, so that devices may follow sleep patterns of themselves according to a predetermined protocol such as a sensor-MAC (WiseMAC) which guarantees that a receiving device is active when data reaches the receiving device.

As described above, the coordinator in the beacon-enabled network is responsible for synchronization of network devices and channel access. In addition, start and end of a superframe are defined by the coordinator. The coordinator has two main features of potential communications from other networks and access to sufficient power supply using, for example, easy change of charged battery.

Data Transmission in IEEE 802.15.4 Network

FIGS. 6 to 9 are flowcharts illustrating data transmission between a device 10 and a coordinator 20 in an IEEE 802.15.4 network.

IEEE 802.15.4 defines three basic transmission types as follows.

1. A device transmits data thereof to a coordinator (uplink transmission).
   : this type is used in both star and peer-to-peer topologies.
2. A coordinator transmits data to a device (downlink transmission).
   : this case is used in both star and peer-to-peer topologies.
3. Data transmission between two peers
   : this case is used only in peer-to-peer topology.

Figure 6:
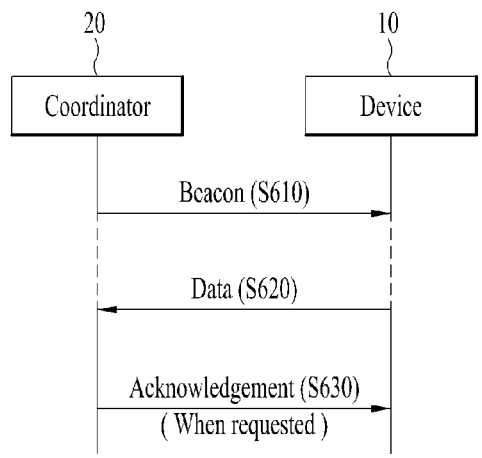
FIGS. 6 to 9 are flowcharts illustrating data transmission between a device and a coordinator in an IEEE 802.15.4 network.
Figure 7:
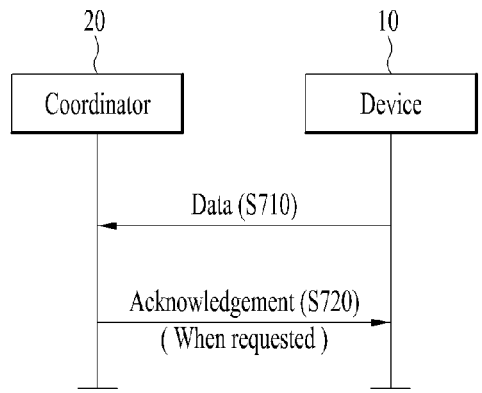

FIG. 6 illustrates uplink data transmission in a beacon-enabled IEEE 802.15.4 network. FIG. 7 illustrates uplink data transmission in a non beacon-enabled IEEE 802.15.4 network.

That is, FIGS. 6 and 7 illustrate data transmission from the device 10 to the coordinator 20 in a beacon-enabled or non beacon-enabled network.

Referring to FIG. 6, in the beacon-enabled network, the device 10 receives a beacon frame from the coordinator 20 (S610) and then transmits data (data frame) to the coordinator 20 using CSMA-CA in a CFP or GTS in a GTS (S620).

On the other hand, referring to FIG. 7, in the non beacon-enabled network, in general, a beacon frame is not present, and the device 10 freely transmits a data frame to the coordinator 20 using CSMA-CA (S710).

Both in FIGS. 6 and 7, the coordinator 20 transmits an optional acknowledgement response frame, that is, ACK (S630 and S720) to acknowledge successful data reception.

When a receiver cannot process the received data frame due to any reason, an acknowledgement message is not transmitted. When a transmitter does not receive acknowledgement after predetermined time elapses, the transmitter assumes that transmission is not successful and retries to transmit a frame. When the transmitter does not receive acknowledgement still despite several retrials, the transmitter may select transaction termination or retrial. When acknowledgement is not requested, the transmitter assumes that the transmission is successful.

Figure 8:
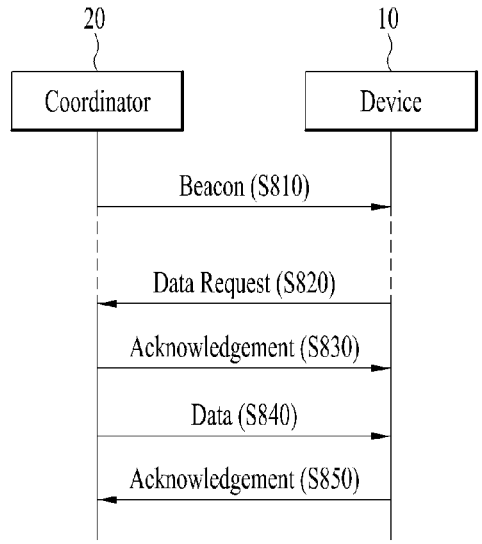
Figure 9:
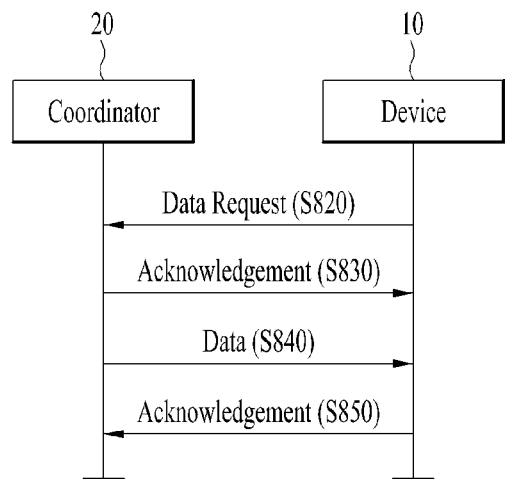

FIG. 8 illustrates downlink data transmission in a beacon-enabled IEEE 802.15.4 network. FIG. 9 illustrates downlink data transmission in a non beacon-enabled IEEE 802.15.4 network.

That is, FIGS. 8 and 9 illustrate data transmission from the coordinator 20 to the device 10 in a beacon-enabled or non beacon-enabled network.

Referring to FIG. 8, in a beacon-enabled WPAN, when the coordinator 20 wants to transmit data to the device 10, the coordinator 20 indicates in a beacon frame that a data message is pending. The device 10 periodically listens to the beacon frame (S810), and transmits a data request (MAC command) using CSMA-CA when the data message is pending (S820). The coordinator 20 transmits an acknowledgement frame to acknowledge successful reception of the data request (S830). Then, the pending data frame is transmitted using slot CSMA-CA or is transmitted immediately after the acknowledgement is transmitted if possible (S840). The device 10 may transmit an optional acknowledgement frame to acknowledge successful data reception (S850). In this case, transaction is terminated. When the data transaction is successfully terminated, the message is removed from a list of pending messages in a beacon.

Referring to FIG. 9, in a non beacon-enabled network, the coordinator 20 having data prepared for a specific device 10 needs to wait for a data request from a related device, which is transmitted based on contention. When the coordinator 20 receives the data request (S910), the coordinator 20 may transmit an acknowledgement frame (which is also used to indicate that data is not prepared) and a data frame subsequent thereto (S920 and S930), and the device 10 may transmit another acknowledgement frame in response to the acknowledgement frame (S940).

IEEE 802.15.4 Frame Format

Figure 10A:
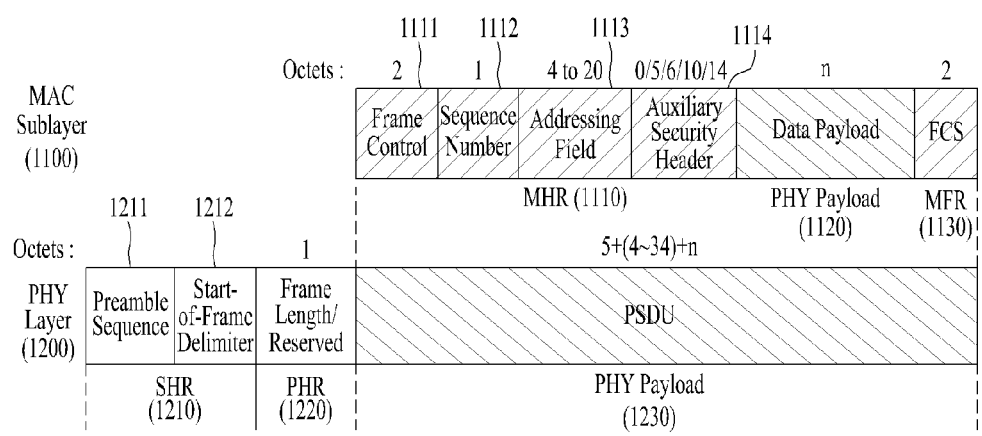
FIG. 10A illustrates an example of each frame format in an IEEE 802.15.4 MAC layer and a PHY layer.

FIG. 10A illustrates an example of each frame format in an IEEE 802.15.4 MAC layer 1100 and a PHY layer 1200.

As illustrated in FIGS. 6 to 9, communication in the IEEE 802.15.4 network involves four different types of frames:
   a beacon frame used to transmit a beacon by a coordinator,
   a data frame used to transmit all data,
   an acknowledgement frame used to acknowledge successful frame reception, and
   a MAC command frame used to manage all MAC peer entity control transmission such as data requests.

The above four types of frames have very similar structures.

Referring to FIG. 10A, a frame format of the MAC layer 1100 includes a MAC header (MHR) 1110, a MAC payload 1120, and a MAC footer (MFR) 1130.

The MHR 1110, the MAC payload 1120, and the MFR 1130 form one MAC data frame (that is, MPDU). The MPDU is a PHY service data unit (PSDU), is transmitted to the PHY layer 1200, and functions as a PHY payload 1230 in the PHY layer 1200. In front of the PHY payload 1230, a synchronization header (SHR) 1210 including a preamble sequence 1211 and a start-of-frame delimiter (SFD) 1212, and a PHY header (PHR) 1220 including the length of the PHY payload 1230 of an octet unit are positioned. The preamble sequence 1211 and the SFD 1212 allow a receiver to achieve symbol synchronization.

The SHR 1210, the PHR 1220, and the PHY payload 1230 form one PHY packet (PHY protocol data unit (PPDU)).

As illustrated in FIG. 10A, the MHR 1110 includes a frame control field 1111, a sequence number field 1112, an addressing field 1113, and an auxiliary security header field 1114.

Among the fields included in the MHR, the frame control field 1111 may contain a value representing a type of frame 1100 format, the sequence number field 1112 may contain a current value of macDSN, and the addressing field 1113 may contain receiving and/or transmitting addresses. In addition, the auxiliary security header field 1114 may contain information required to process security process of the frame 1100.

The MAC payload 1120 may include a command frame identifier and a command payload.

In addition, the MFR 1130 may include a frame check sequence 1130 (hereinafter, referred to as FCS). The FCS may be used to determine whether an error of data transmission arises with respect to the MHR 1110 and the MAC payload 1120.

Here, the beacon frame, the acknowledgement frame, and the MAC command frame have similar structures, except that the MAC payload has different functions in the respective cases and the acknowledgement frame does not have the MAC payload. In addition, the beacon frame, the acknowledgement frame, and the MAC command frame are originated in the MAC layer 1100 without any interference of upper layers.

Beacon Frame Format of IEEE 802.15.4

FIG. 10B illustrates an example of a format of a beacon frame 600 of IEEE 802.15.4 to which an embodiment of the present invention is applicable.

As illustrated in FIG. 10B, the beacon frame 600 includes the MHR 1110, the MAC payload 1120, and the MFR 1130 of FIG. 10A.

In addition, the MAC payload 1120 of the beacon frame 600 may include a superframe specification field 1121, a GTS specification field 1122, a GTS direction field 1123, a GTS list field 1124, a pending address field 1125, and a beacon payload field 1126.

The superframe specification field 1121 may include a beacon order, a superframe order, a last CAP slot, information of battery lifetime, and information regarding whether transmission from a PAN coordinator is performed.

The GTS specification field 1122, the GTS direction field 1123, and the GTS list field 1124 may be collectively referred to as GTS fields.

The GTS specification field 1122 may include a GTS descriptor count sub field. The GTS descriptor count sub field may represent the number of GTS descriptors to be included in the GTS list field 1124. For example, when the size of the GTS descriptor count sub field is 3 bits, the GTS list field 1124 may include maximum of 7 GTS descriptors.

The GTS direction field 1123 may include a GTS direction mask sub field representing a direction of GTSs included in the subframe. That is, the GTS direction mask sub field may include information regarding whether each GTS included in the GTS list field 1124 is used for transmit-only or receive-only.

The GTS list field 1124 may include a GTS descriptor field including GTS allocation information. The GTS list field 1124 may include one or more GTS descriptor fields according to a value indicated by the GTS descriptor count sub field. In addition, whether the GTS descriptor field is used for transmit-only or receive-only may be determined according to the GTS direction mask sub field.

The GTS descriptor field included in the GTS list field 1124 may include a device short address field 1124-1, a GTS starting slot field 1124-2, a GTS length field 1124-3, a start sequence number 1124-4, a GTS interval field 1124-5, and a GTS window field 1124-6, as illustrated in FIG. 10B.

The device short address field 1124-1 represents an address of a device to which GTS is allocated by the GTS descriptor. That is, when the GTS related to the GTS descriptor field is allocated to the device 10, the device short address field 1124-1 has an address of the device 10.

The GTS starting slot field 1124-2 represents information regarding a superframe slot when GTS is started.

The GTS length field 1124-3 represents the number of GTSs that are consecutively activated in a superframe.

The GTS interval field 1124-5 represents a number for determination of the number of superframes to which GTS is allocated at regular intervals. The GTS interval field 1124-5 may have a value representing an interval between superframes to which GTS is allocated or a specific time value to which GTS is allocated.

The GTS window field 1124-6 represents a number indicating a range which is determined by the GTS interval field 1124-5 and to which GTS is allocated before and after a superframe.

Frame Control Field of IEEE 802.15.4

FIG. 11 is a diagram illustrating an example of a frame control field in the frame format illustrated in FIG. 10A.

A frame control field used in each frame type is illustrated in FIG. 10A in more detail. As illustrated in FIG. 11, the frame control field consists of 16 bits allocated to sub fields for different purposes. In detail, first three bits of the field represent a frame type, that is, a beacon frame, a data frame, an acknowledgement frame, or a MAC command frame. A method of indicating the frame type is illustrated in FIG. 10B. Subsequent to the frame type bit, a single-bit security enabled sub field representing whether security is enabled by a MAC sub layer is positioned. Subsequent to the single-bit security enabled sub field, a frame pending sub field representing whether a transmitter has additional data for a receiver is positioned. Subsequent to the frame pending sub field, an ACK. Request sub field representing whether acknowledgement is requested by the receiver is positioned. Subsequent to the ACK. Subsequent to the ACK. Request sub field, additional predetermined sub fields used for reservation or addressing in the current IEEE 802.15.4 standard is positioned.

Table 1 below shows an example of a frame type value in the frame control field of FIG. 11.

TABLE 1

| Frame type value (b2b1b0) | Description |
| --- | --- |
| 000 | Beacon |
| 001 | Data |
| 010 | Acknowledgement |
| 011 | MAC command |
| 100-111 | Reservation |

MAC Command Frame Format of IEEE 802.15.4

FIG. 12 illustrates an example of a MAC command frame format of IEEE 802.15.4 to which an embodiment of the present invention is applicable.

As illustrated in FIG. 12, a MAC payload may include a command frame identifier and a command payload.

Among the fields included in the MAC payload, the command frame identifier represents a type of the command frame.

Table 2 below shows an example of a command frame identifier in the MAC command frame format of FIG. 12.

TABLE 2

| Command frame identifier | Command name | RFD Tx | RFD Rx |
| --- | --- | --- | --- |
| 0x01 | Association request | X | |
| 0x02 | Association response | | X |
| 0x03 | Deassociation notification | X | X |
| 0x04 | Data request | X | |
| 0x05 | PAN ID conflict notification | X | |
| 0x06 | Orphan Notification | X | |
| 0x07 | Beacon request | | |
| 0x08 | Coordinator realignment | | X |
| 0x09 | GTS request | | |
| 0x0a to 0xff | Reservation | | |

When the command frame identifier represents a GTS request command for GTS allocation request, that is, when the command frame identifier is '0x09', the command payload may be a value representing GTS characteristics. The GTS characteristic value includes values representing the GTS characteristics requested to the coordinator 20 by the device 10.

To this end, the GTS characteristic value may include a GTS length field, a GTS direction field, a characteristics type field, a GTS interval field, and a GTS window field.

Hereinafter, a method in which a terminal proposed according to the disclosure associates with a base station at a band of 2390 MHz to 2400 MHz and receives an available channel list of a band of 2360 MHz to 2390 MHz to reform association with the base station via a channel of a band of 2360 MHz to 2390 MHz will be described in detail.

First, it is assumed that an MBAN system uses a non beacon-enabled network in a band of 2360 MHz to 2390 MHz and uses a beacon-enabled network in a band of 2390 MHz to 2400 MHz.

Figure 13:
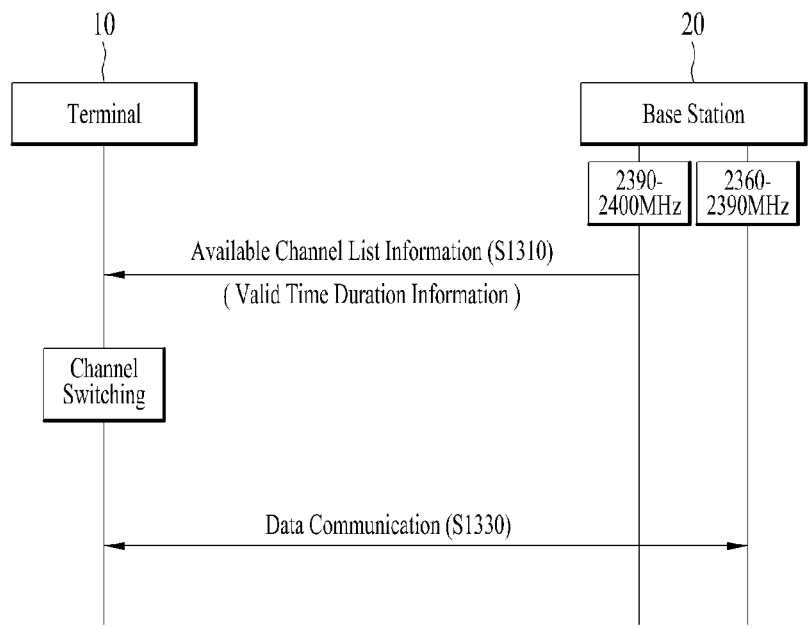
FIG. 13 is a flowchart of a method of setting association between a terminal and a base station in an MBAN system proposed according to the disclosure.

FIG. 13 is a flowchart of a method of setting association between a terminal 10 and a base station 20 in an MBAN system proposed according to the disclosure.

Referring to FIG. 13, the a terminal 10 (for example, a MBAN terminal or device) receives information of an available channel list representing at least one channel that is available in a second frequency band via a channel of a frequency band 2390 MHz to 2400 MHz from the base station 20 (for example, an AP or a coordinator) (S1310). Here, the available channel list information may be received via a beacon frame or a separate message. Embodiments in which the available channel list information is transmitted will be described below with reference to FIGS. 14 to 16 in detail.

In addition, the terminal 10 may further receive information of a valid time duration representing available time of each available channel in the second frequency band in operation S1310. Here, the valid time duration information may be further received from the base station 20. Here, the valid time duration information may be received together with the available channel list information or after the available channel list information is received.

The first frequency band refers to a frequency band in the range of 2390 MHz to 2400 MHz, the second frequency band refers to a frequency band in the range of 2360 MHz to 2390 MHz, and the available channel or a channel has a unit of 5 MHz.

In addition, the available channel list information (a field or a parameter) may include a bitmap form, a center frequency and bandwidth of each available channel, or a start frequency and last frequency form of each available channel.

The number of available channels present in the first frequency band is six from a channel 1 to a channel 6. Thus, when the available channel list information corresponds to a bitmap form, the bitmap consists of 6 bits (bit 0 to 5 or bit 2 to 7).

For example, when a channel 2 and a channel 4 can be used among the six channels from the channel 1 to the channel 6 in the first frequency band, the available channel list information may be represented in a bitmap form of '010100xx'. Here, 'xx' represents an arbitrary value, '0' represents a channel that cannot be used in the first frequency band, and '1' represents a channel that can be used in the first frequency band, that is, an available channel. Here, '0' and '1' may be defined vice versa.

For another example, when the available channel list information has center frequency=2365 and bandwidth=4, this means that a channel of 2363 MHz to 2367 MHz can be used. In addition, when the available channel list information has start frequency=2363 and end frequency=2367, the channel of 2363 MHz to 2367 MHz can also be used.

In addition, the number of bits required by the available channel list information is changed according to channelization, and thus, the length of the available channel list information may be increased.

Then, the terminal 10 performs channel switching to an available channel of the second frequency band from a channel of the first frequency band based on the received available channel list information (S1320). Here, when the terminal 10 performs the channel switching, the terminal 10 may terminate association with the base station 20 in the first frequency band.

Then, the terminal 10 transmits and receives data to and from the base station 20 via the available channel of the second frequency band (S1330).

First Embodiment

A first embodiment of the disclosure provides a method of transmitting the available channel list information illustrated in FIG. 13 via a separate message.

Figure 14:
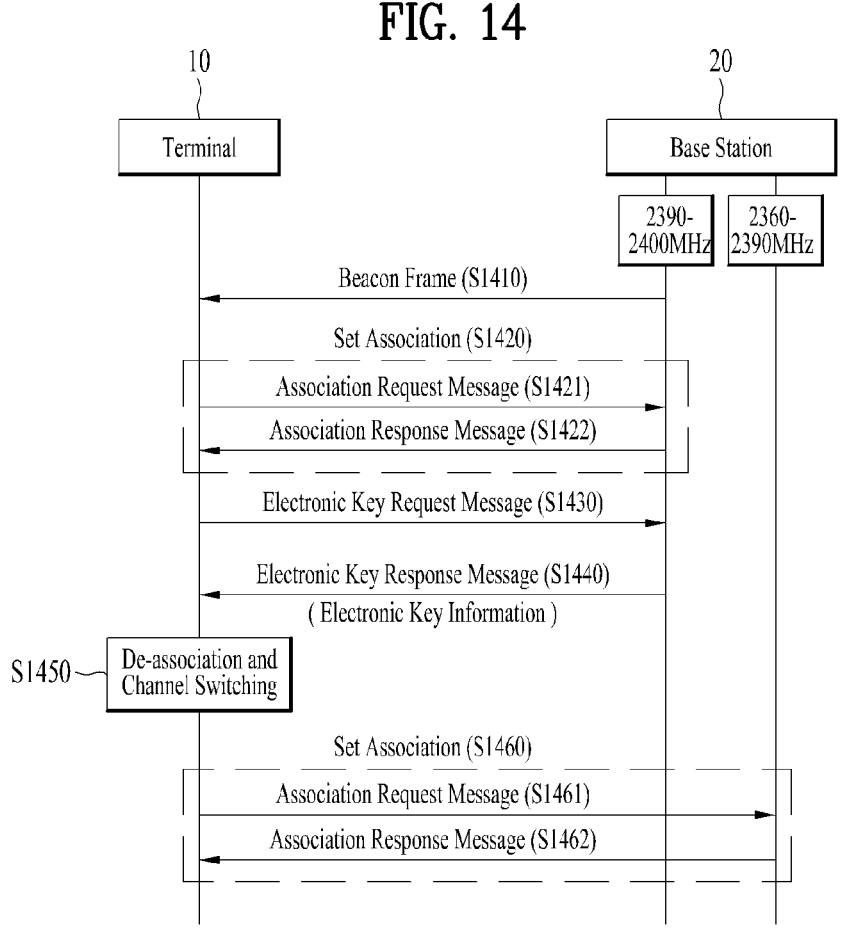
FIG. 14 is a flowchart of a method of transmitting available channel list information according to a first embodiment of the disclosure.

FIG. 14 is a flowchart of a method of transmitting available channel list information according to the first embodiment of the disclosure.

Referring to FIG. 14, a terminal 10 receives a beacon frame from a base station 20 via a channel in a first frequency band (S1410). Here, the terminal 10 searches for an MBAN network via passive scanning in the first frequency band in order to enter the MBAN network. Here, the terminal 10 may receive the beacon frame for each respective channel in the first frequency band.

In addition, the beacon frame may be transmitted to the terminal 10 in a broadcast manner. The beacon frame includes information regarding the MBAN network.

Then, the terminal 10 associates with the base station 20 (S1420).

That is, the terminal 10 transmits an association request message (or an association request frame) to the base station 20 (S1421). The base station 20 that receives the association request message determines whether the terminal 10 that transmitted the association request message is appropriate and then transmits an association response message (or an association response frame) including a result of the determination to the terminal 10 (S1422).

When the association between the terminal 10 and the base station 20 is set, the terminal and the base station transmit and receive data via a channel in the first frequency band.

Then, the terminal 10 transmits an electronic key (E-key) request message (or an E-key request frame) to the base station 20 in order to acquire E-key information related to an available channel of the second frequency band (S1430).

Here, the E-key information may include an available channel list field, a valid time field, a personal area network identifier (PAN ID) field, and a transmission power limitation field.

The available channel list field represents a list of channels that can be used in the second frequency band. The valid time field represents available time for each respective channel in the first frequency band.

The PAN ID field represents an identifier of a WPAN network that uses a specific channel of the first frequency band.

The transmit power limit field represents maximum transmission power in a specific channel of the first frequency band.

Then, the base station 20 transmits an E-key response message including the E-key information to the terminal 10 (S1440).

Then, the terminal 10 sets deassociation with the base station 20 in the first frequency band and performs channel switching to any one channel in the second frequency band according to the E-key information (S1450).

Then, the terminal 10 forms (or sets) association with the base station 20 via the switched channel of the second frequency band (S1460). That is, the terminal 10 may set association in the second frequency band without receiving a beacon frame from the base station 20.

Here, the association setting in operation S1460 is performed by transmitting the association request message from the base station 20 and receiving the association response message from the base station 20, like in operation S1420 (S1461 and S1462).

Second Embodiment

A second embodiment of the disclosure provides another method of transmitting the available channel list information illustrated in FIG. 13 via a separate message.

That is, the second embodiment provides a method of transceiving data in the second frequency band by receiving E-key information from the base station 20 and performing switching to a channel in the second frequency channel without operation S1420 according to the first embodiment, that is, an operation of setting association between the terminal 10 and the base station 20 in the first frequency band.

Figure 15:
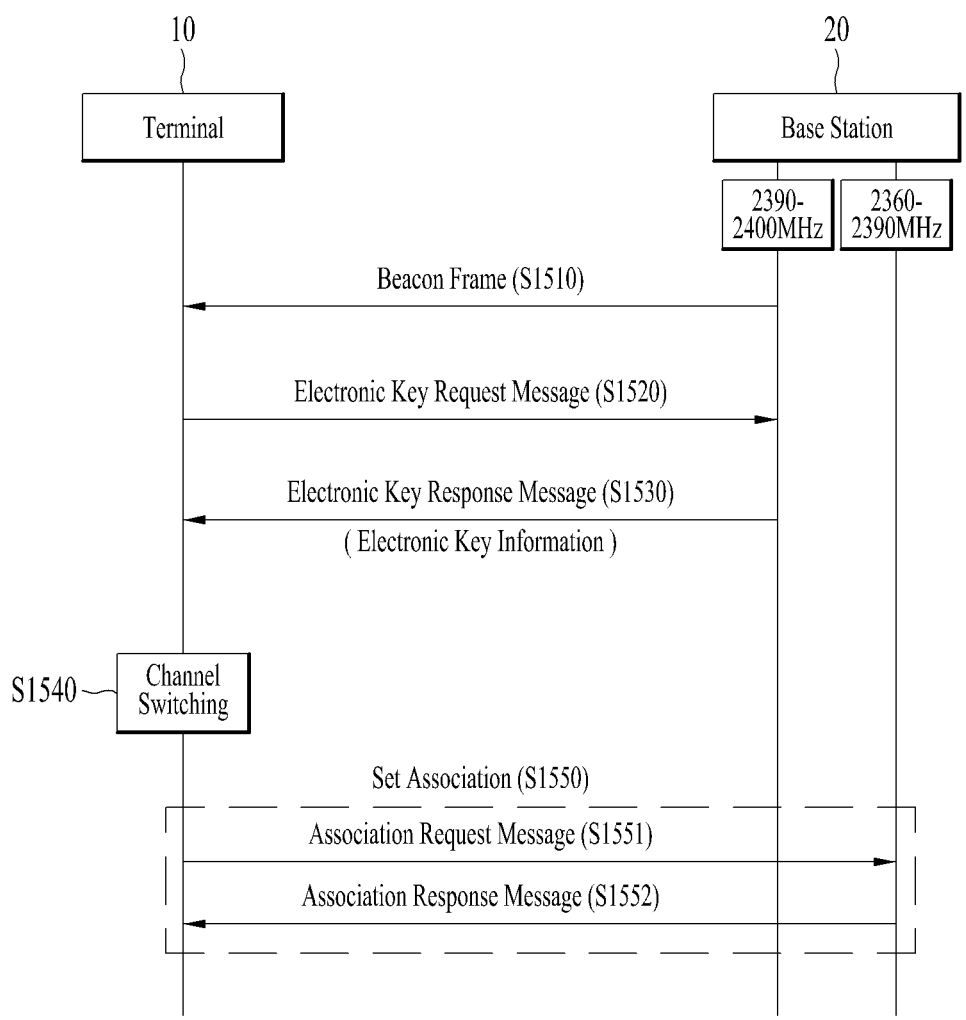
FIG. 15 is a flowchart of a method of transmitting available channel list information according to a second embodiment of the disclosure.

FIG. 15 is a flowchart of a method of transmitting available channel list information according to the second embodiment of the disclosure.

Referring to FIG. 15, the terminal 10 receives a beacon frame from the base station 20 via a channel in the first frequency band (S1510).

Then, the terminal 10 transmits an E-key request message from the base station 20 in order to acquire E-key information from the base station 20 (S1520). Here, the E-key information represents information related to an available channel in the second frequency band, as described above.

Then, the terminal 10 receives an E-key response message including the E-key information from the base station 20 (S1530).

Then, the terminal 10 performs channel switching to an available channel in the second frequency band based on the E-key information (S1540).

Then, the terminal 10 forms (or sets) association with the base station 20 via the switched channel in the second frequency band and then transmits and receives data to and from the base station 20 (S1550). Here, operation S1550 (including operations S1551 and S1552) is the same as operation S1460 of FIG. 14.

Third Embodiment

A third embodiment of the disclosure provides a method of transmitting the available channel list information illustrated in FIG. 13 via a beacon frame.

Figure 16:
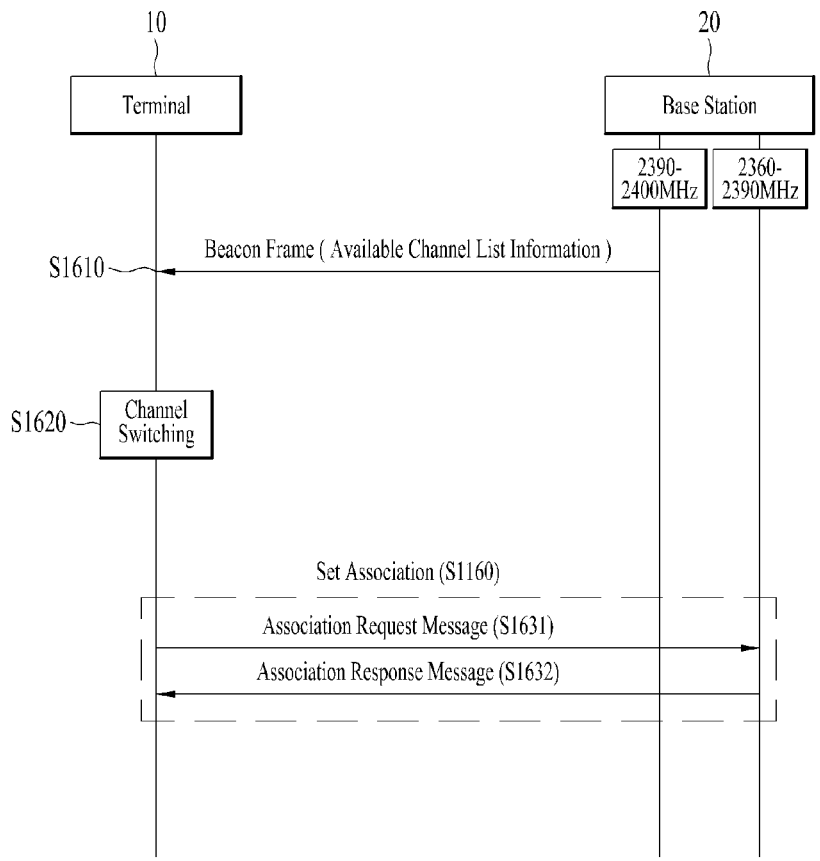
FIG. 16 is a flowchart of a method of transmitting available channel list information according to a third embodiment of the disclosure.

FIG. 16 is a flowchart of a method of transmitting available channel list information according to the third embodiment of the disclosure.

Referring to FIG. 16, the terminal 10 receives a beacon frame including available channel list information (a field or a parameter) representing at least one channel that can be used in the second frequency band from the base station 20 in the first frequency band (S1610).

Here, the available channel list information may be included in a MAC payload of the beacon frame or may include an independent field of the beacon frame.

Here, in case of MBAN system that assumes a contention-based protocol, the length of CFP, that is a contention free duration of the beacon frame may be 0.

In addition, an available channel in the first frequency band may vary over time, and thus, the beacon frame may further include valid time duration information representing available time of each available channel in the second frequency band. Here, the valid time duration information may be positioned immediately after the available channel list information. In addition, the length of the valid time duration information may be set to different values according to resolution of the time duration.

For another example, the beacon frame may not include the available channel list information and may include only the valid time duration information.

In reality, when time taken for the terminal 10 to scan a channel for transmission of the base station 20 barely affects overall battery loss, the base station 20 may not transmit the available channel list information to the terminal 10.

Here, the valid time duration information may be included in a MAC payload of the beacon frame or may include an independent field of the beacon frame.

In addition, a value of the valid time duration information may be changed according to system deployment, and thus, may be 2 octet or more.

Then, the terminal 10 selects any one available channel among available channels in the second frequency band based on the available channel list information and performs channel switching to the selected available channel (S1620).

Then, the terminal 10 sets association with the base station 20 via the channel-switched available channel (S1630).

Here, operation S1630 (including operations S1631 and S1632) of setting the association is the same as operation S1550 of FIG. 15.

Then, when the terminal 10 transmits a data request message to the base station 20 and receives ACK of the data request message from the base station 20 in order to receive downlink data, the terminal 10 receives the downlink data from the base station 20.

In case of uplink transmission, when the terminal 10 has data to be transmitted to the base station 20, the terminal 10 transmits uplink data to the base station 20. Here, the base station 20 may transmit ACK of the uplink data to the terminal 10 for reliability.

Figure 17:
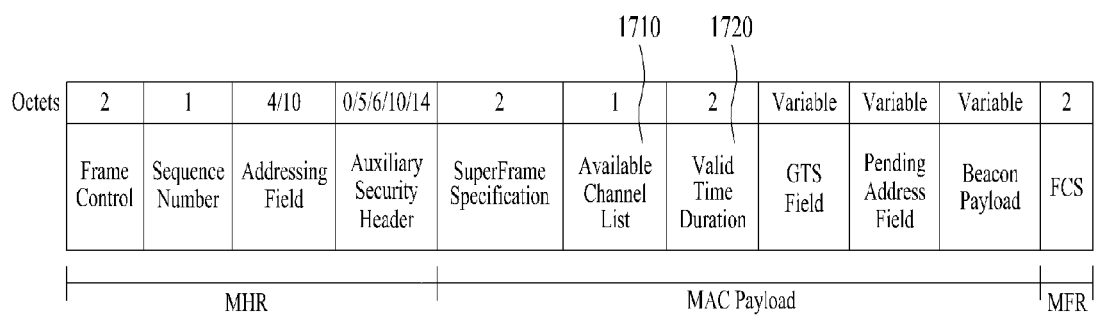
FIG. 17 illustrates a view illustrating an example of a beacon frame format including the available channel list information and the valid time duration information.

FIG. 17 illustrates a view illustrating an example of a beacon frame format including the available channel list information and the valid time duration information.

As seen from FIG. 17, the beacon frame may include available channel list information 1710 and valid time duration information 1720 in a MAC payload.

As described above, each of the available channel list information and the valid time duration information may not be contained in the MAC payload of the beacon frame and may include an independent field.

The above-described embodiments and modified embodiments may be combined with each other, and thus, may be used alone or in combination thereof, as necessary. The combination may be easily implemented by one of ordinary skill in the art, and thus, a detailed description thereof will not be given here. Although not described, it is to be appreciated that the combination is not precluded, and is within the scope of the invention.

The embodiments of the present invention may be achieved by various means, for example, hardware, firmware, software, or a combination thereof.

In a hardware configuration, an embodiment of the present invention may be achieved by one or more application specific integrated circuits (ASICs), digital signal processors (DSPs), digital signal processing devices (DSPDs), programmable logic devices (PLDs), field programmable gate arrays (FPGAs), processors, controllers, microcontrollers, microprocessors, etc.

In a firmware or software configuration, an embodiment of the present invention may be implemented in the form of a module, a procedure, a function, etc. Software code may be stored in a memory unit and executed by a processor. The memory unit is located at the interior or exterior of the processor and may transmit and receive data to and from the processor via various known means.

For example, the methods according to the present invention may be stored in a storage medium (e.g., an internal memory, a flash memory, a hard disk, etc.) and may be implemented as code or commands in a software program that can be executed by a processor (e.g., a microprocessor), which will be described with reference to FIG. 18.

Figure 18:
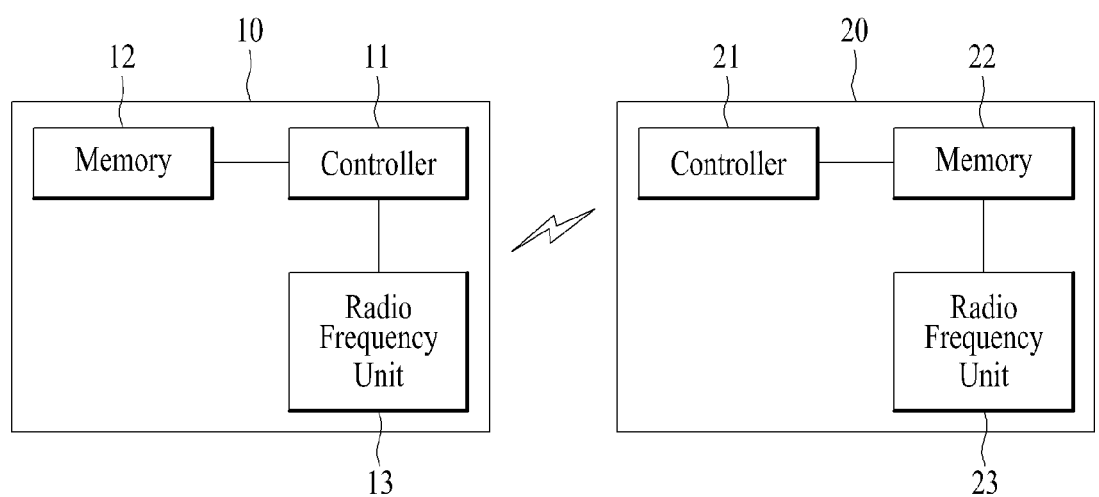
FIG. 18 is an internal block diagram of a terminal and a base station in a MBAN system to which an embodiment of the disclosure is applicable.

FIG. 18 is an internal block diagram of the terminal 10 and the base station 20 in a MBAN system to which an embodiment of the disclosure is applicable.

The terminal 10 includes a controller 11, a memory 12, and a radio frequency (RF) unit 13.

In addition, the terminal 10 includes a display unit, a user interface unit, etc.

The controller 11 performs suggested functions, processes, and/or methods. Layers of a wireless interface protocol are embodied by the controller 11.

The memory 12 is connected to the controller 11 and stores a protocol or parameter for performing wireless communication. That is, the memory 12 stores a terminal driving system, application, and general files.

The RF unit 13 is connected to the controller 11 and transmits and/or receives radio signals.

Furthermore, the display unit may display various information of the terminal 10 and may use a well-known element such as a liquid crystal display (LCD), an organic light emitting diode (OLED), etc. The user interface unit may be configured by a combination of well-known user interfaces such as a keypad, a touchscreen, etc.

The base station 20 includes a controller 21, a memory 22, and an RF unit 23.

The controller 21 performs suggested functions, processes, and/or methods. Layers of a wireless interface protocol stack may be embodied by the controller 21.

The memory 22 is connected to the controller 21 and stores a protocol or parameter for performing wireless communication.

The RF unit 23 is connected to the controller 21 and transmits and/or receives radio signals.

The controllers 11 and 21 may include an application-specific integrated circuit (ASIC), another chip set, a logic circuit, and/or data processing device. The memories 12 and 22 may include a read-only memory (ROM), a random access memory (RAM), a flash memory, a memory card, a storage medium, and/or another storage device. The RF units 13 and 23 may include a baseband circuit for processing radio signals. When an embodiment is embodied via software configuration, the aforementioned scheme may be embodied by a module (a process, a function, etc.) for performing the aforementioned function. The module may be stored in the memories 12 and 22 and may be executed by the controllers 11 and 21.

The memories 12 and 22 may be disposed inside or outside the controllers 11 and 21 and may be connected to the controllers 11 and 21 by well-known means.

The invention claimed is:

1. A method of transmitting and receiving data by a terminal with a base station in a medical body area network (MBAN), the method comprising:
    receiving available channel list information from the base station via a channel of a first frequency band, the available channel list information indicating at least one available channel of a second frequency band;
    performing channel switching from the channel of the first frequency band to one of the at least one available channel of the second frequency band, based on the available channel list information; and
    communicating data with the base station via the channel-switched available channel,
    wherein receiving the available channel list information includes:
    receiving a beacon frame from the base station via the channel of the first frequency band,
    transmitting to the base station an electronic key request message for requesting available channel information of the second frequency band, and
    receiving from the base station an electronic key response message in response to the electronic key request message,
    wherein the available channel list information is contained in the electronic key response message, and
    wherein the electronic key response message comprises personal area network identifier (PAN ID) information representing a wireless personal area network (WPAN) using a specific channel of the second frequency band, and transmit power limit information representing maximum transmission power in the specific channel of the second frequency band.

2. The method according to claim 1, wherein the communicating of the data comprises setting association with the base station,
    wherein the setting of the association comprises transmitting an association request message to the base station, and receiving an association response message corresponding to the association request message from the base station.

3. The method according to claim 1, wherein the available channel list information is received via the beacon frame.

4. The method according to claim 1, further comprising setting association with the base station in the first frequency band,
    wherein the setting of the association comprises transmitting an association request message to the base station via the channel of the first frequency band; and
    receiving an association response message corresponding to the association request message from the base station via the channel of the first frequency band.

5. The method according to claim 1, wherein the available channel list information comprises information regarding a bitmap, a center frequency and bandwidth of each available channel, or a start frequency and end frequency of each available channel.

6. The method according to claim 1, wherein the available channel list information is included in a MAC payload of the beacon frame.

7. The method according to claim 1, further comprising receiving from the base station valid time duration information representing available time of an available channel of the second frequency band.

8. The method according to claim 7, wherein the valid time duration information is received after the available channel list information.

9. The method according to claim 1, wherein the first frequency band is in a range of 2390 MHz to 2400 MHz, the second frequency band is in a range of 2360 MHz to 2390 MHz, and the channel has 5 MHz.

10. A terminal for transmitting and receiving data with a base station in a medical body area network (MBAN), the terminal comprising:
   a radio frequency unit for transmitting and receiving a radio signal; and
   a controller connected to the radio frequency unit, wherein the controller controls the radio frequency unit to receive available channel list information via a channel of a first frequency band, the available channel list information indicating at least one available channel of a second frequency band, performs channel switching from the channel of the first frequency band to one of the at least one available channel of the second frequency band, based on the available channel list information, and controls the radio frequency unit to communicate data with the base station via the channel-switched available channel,
   wherein receiving the available channel list information includes:
   receiving a beacon frame from the base station via the channel of the first frequency band,
   transmitting to the base station an electronic key request message for requesting available channel information of the second frequency band, and
   receiving from the base station an electronic key response message in response to the electronic key request message,
   wherein the available channel list information is contained in the electronic key response message, and
   wherein the electronic key response message comprises personal area network identifier (PAN ID) information representing a wireless personal area network (WPAN) using a specific channel of the second frequency band, and transmit power limit information representing maximum transmission power in the specific channel of the second frequency band.

11. The terminal according to claim 10, wherein the controller controls the radio frequency unit to receive from the base station valid time duration information representing available time of an available channel of the second frequency band.

12. The terminal according to claim 11, wherein the valid time duration information is received after the available channel list information.

13. The terminal according to claim 10, wherein the first frequency band is in a range of 2390 MHz to 2400 MHz, the second frequency band is in a range of 2360 MHz to 2390 MHz, and the channel has 5 MHz.

14. The terminal according to claim 10, wherein the communicating of the data y the radio frequency unit comprises setting association with the base station,
   wherein the setting of the association comprises transmitting an association request message to the base station, and receiving an association response message corresponding to the association request message from the base station.

15. The terminal according to claim 10, wherein the available channel list information is received via the beacon frame.

16. The terminal according to claim 10, wherein the controller sets association with the base station in the first frequency band,
   wherein the setting of the association comprises transmitting an association request message to the base station via the channel of the first frequency band; and
   receiving an association response message corresponding to the association request message from the base station via the channel of the first frequency band.

17. The terminal according to claim 10, wherein the available channel list information comprises information regarding a bitmap, a center frequency and bandwidth of each available channel, or a start frequency and end frequency of each available channel.

18. The terminal according to claim 10, wherein the available channel list information is included in a MAC payload of the beacon frame.

* * * * *